United States Patent
Richards

(10) Patent No.: US 11,246,812 B2
(45) Date of Patent: Feb. 15, 2022

(54) COMPOSITIONS AND METHODS FOR THE TREATMENT OF CELLULITE

(71) Applicant: Reoxcyn, LLC, Ogden, UT (US)

(72) Inventor: Kurt Richards, Herriman, UT (US)

(73) Assignee: REOXCYN, LLC, Ogden, UT (US)

( * ) Notice: Subject to any disclaimer, the term of this patent is extended or adjusted under 35 U.S.C. 154(b) by 0 days.

(21) Appl. No.: 16/173,917

(22) Filed: Oct. 29, 2018

(65) Prior Publication Data

US 2019/0192392 A1    Jun. 27, 2019

Related U.S. Application Data

(60) Provisional application No. 62/609,899, filed on Dec. 22, 2017.

(51) Int. Cl.

| | | |
|---|---|---|
| *A61K 8/20* | (2006.01) | |
| *A61K 8/19* | (2006.01) | |
| *A61K 8/24* | (2006.01) | |
| *A61K 8/25* | (2006.01) | |
| *A61K 8/891* | (2006.01) | |
| *A61Q 19/06* | (2006.01) | |
| *A61K 8/96* | (2006.01) | |
| *A61K 8/58* | (2006.01) | |

(52) U.S. Cl.
CPC .................. *A61K 8/20* (2013.01); *A61K 8/19* (2013.01); *A61K 8/24* (2013.01); *A61K 8/25* (2013.01); *A61K 8/585* (2013.01); *A61K 8/891* (2013.01); *A61K 8/965* (2013.01); *A61Q 19/06* (2013.01)

(58) Field of Classification Search
CPC ...................................................... A61Q 19/06
See application file for complete search history.

(56) References Cited

U.S. PATENT DOCUMENTS

| | | | |
|---|---|---|---|
| 2004/0181210 A1* | 9/2004 | Shellman | A61N 5/0616 606/8 |
| 2009/0035398 A1* | 2/2009 | Williams | A61K 8/922 424/735 |
| 2009/0209651 A1 | 8/2009 | Seigner et al. | |
| 2011/0305781 A1* | 12/2011 | Hwang | A61K 8/97 424/752 |
| 2016/0317577 A1* | 11/2016 | Hoover | A61K 33/14 |
| 2019/0231911 A1* | 8/2019 | Moroney | A61L 27/306 |

FOREIGN PATENT DOCUMENTS

| | | |
|---|---|---|
| JP | 2008-533152 A | 8/2008 |
| JP | 2014-180235 | 9/2014 |
| JP | 2019-112386 A | 7/2019 |
| KR | 10-2007-0017746 | 2/2007 |
| WO | WO 2006/099385 A2 | 9/2006 |

OTHER PUBLICATIONS

Office Action dated Oct. 22, 2018 and received in JP application No. 2018-99479, which is related to the present application.
Simple Diet Diary, Shake's Simple Diet Experience Note, [online], 2007, [Searched on Oct. 12, 2018], The Internet <URL:http://okigarudiet.livedoor.biz/archives/cat_50042793.html>.
Decision of Rejection issued in JP application No. 2019-133610, dated Dec. 14, 2020.
"Ingredient Comparison", [online], 2014, [Searched Jan. 25, 2019], Internet <URL: https://web.archive.org/web/20141111072444/http://www.slowfood.co.jp/encyclopedia (Newly-cited Publication; Publication showing well-known technology).

* cited by examiner

*Primary Examiner* — Michael B. Pallay
(74) *Attorney, Agent, or Firm* — Knobbe, Martens, Olson & Bear LLP

(57) ABSTRACT

Described herein are methods and formulations for treating, inhibiting, or ameliorating cellulite. Aspects described herein relate to formulations including a saline solution, reactive oxygen species, a rheology agent, an emollient, and a pH modifier and methods of using these formulations for treating, ameliorating, or inhibiting cellulite.

17 Claims, No Drawings

COMPOSITIONS AND METHODS FOR THE TREATMENT OF CELLULITE

CROSS-REFERENCE TO RELATED APPLICATIONS

This application claims priority to U.S. Prov. App. No. 62/609,899, filed Dec. 22, 2017 entitled "COMPOSITIONS AND METHODS FOR THE TREATMENT OF CELLULITE" which is incorporated by reference herein in its entirety.

FIELD

The present disclosure relates to methods and compositions for treating, reducing, inhibiting, or ameliorating cellulite or the appearance of cellulite. Specifically, the present disclosure relates to formulations including a saline solution, a reactive oxygen species, a rheology agent, an emollient, and a pH modifying agent for treating cellulite, and methods of using the cellulite treatment formulations to treat, prevent, reduce, or ameliorate cellulite or an appearance of cellulite.

BACKGROUND

Cellulite is a skin condition often described as an "orange peel," "mattress," "cottage cheese," or "dimpling" appearance on the thighs, buttocks and sometimes lower abdomen and upper arms of otherwise healthy women. Cellulite is caused by small protrusions of fat called papillae adiposae into the dermis. This structural alteration of subcutaneous fat protruding (or herniating) into the dermis gives skin the bumpy appearance referred to as cellulite. Individuals with cellulite and higher BMIs have a weaker, less dense connective tissue structure, leading to increased extrusion of adipose tissue lobules through the hypodermis.

SUMMARY

The present disclosure is directed to compositions and methods for treating, preventing, reducing, or ameliorating cellulite or the appearance of cellulite.

Some embodiments provided herein relate to a method of reducing an appearance of cellulite in a subject in need thereof. In some embodiments, the method includes identifying a region of a body having cellulite. In some embodiments, the method further includes topically applying to the region of the body a composition for treating cellulite. In some embodiments, the composition includes a saline solution, a reactive oxygen species, a rheology agent, an emollient, and a pH modifier. In some embodiments, the method reduces the appearance of cellulite. In some embodiments, the method further includes massaging the composition into the region of the body having cellulite until absorbed. In some embodiments, the composition is administered daily to the region of the body having cellulite.

In some embodiments, reducing the appearance of cellulite includes increasing skin elasticity. In some embodiments, reducing the appearance of cellulite includes reducing subcutaneous fat nodularity. In some embodiments, reducing the appearance of cellulite includes increasing lipolysis in adipocytes.

In some embodiments, the composition includes salt in an amount of about 0.01% to about 1% w/v; hypochlorite in an amount of about 50 to about 100 ppm; sodium magnesium silicate in an amount of about 0.5% to about 10% w/v; dimethicone in an amount of about 0.5% to about 10% w/v; and sodium phosphate monobasic in an amount of about 0.05% to about 5% w/v. In some embodiments, the salt is purified or refined salt, such as table salt. In some embodiments, the salt is raw, unprocessed salt. In some embodiments, the salt is Himalayan sea salt.

Some embodiments provided herein relate to a cellulite treatment formulation. In some embodiments, the formulation includes a saline solution, a reactive oxygen species, a rheology agent, an emollient, and a pH modifier.

In some embodiments, the saline solution includes salt in an amount of about 0.01% to about 1% w/v, such as 0.01%, 0.02%, 0.03%, 0.04%, 0.05%, 0.06%, 0.07%, 0.08% 0.09%, 0.1%, 0.2%, 0.3%, 0.4%, 0.5%, 0.6%, 0.7%, 0.8%, 0.9%, or 1% or an amount within a range defined by any two of the aforementioned values. In some embodiments, the salt is present in an amount of about 0.05% w/v. In some embodiments, the salt is present in an amount of about 0.05% w/w. In some embodiments, the salt is purified or refined salt, such as table salt. In some embodiments, the salt is raw, unprocessed salt. In some embodiments, the salt is Himalayan sea salt.

In some embodiments, the reactive oxygen species is hypochlorite. In some embodiments, the reactive oxygen species is present in an amount of about 25 to about 100 ppm. In some embodiments, the reactive oxygen species is present in an amount of about 72 ppm. In some embodiments, the reactive oxygen species is present in an amount of about 0.16% w/w.

In some embodiments, the rheology agent is a metal silicate. In some embodiments, the metal silicate is sodium magnesium silicate. In some embodiments, the rheology agent is present in an amount of about 0.5% to about 10% w/v. In some embodiments, the rheology agent is present in an amount of about 3.25% w/v. In some embodiments, the rheology agent is present in an amount of about 3.14% w/w.

In some embodiments, the emollient is a silicone polymer. In some embodiments, the silicone polymer is dimethicone, cyclomethicone, or a blend thereof. In some embodiments, the emollient is present in an amount of about 0.5% to about 10% w/v. In some embodiments, the emollient is present in an amount of about 5% w/v. In some embodiments, the emollient is present in an amount of about 0.93% w/w.

In some embodiments, the pH modifier is sodium phosphate monobasic. In some embodiments, the pH modifier is present in an amount of about 0.05% to about 5% w/v. In some embodiments, the pH modifier is present in an amount of about 0.3% w/v. In some embodiments, the pH modifier is present in an amount of about 0.19% w/w.

In some embodiments, the formulation is in the form of a cream, foam, gel, serum, lotion, mousse, ointment, paste, serum, solution, spray, stick, or suspension.

Some embodiments provided herein relate to a cellulite treatment formulation. In some embodiments, the formulation includes salt in an amount of about 0.05% w/v, hypochlorite in an amount of about 72 ppm, sodium magnesium silicate in an amount of about 3.25%, dimethicone in an amount of about 5%, and sodium phosphate monobasic in an amount of about 0.3% w/v.

Some embodiments provided herein relate to a cellulite treatment formulation. In some embodiments, the formulation includes salt in an amount of about 0.05% w/w, a reactive oxygen species in an amount of about 0.16% w/w, a metal silicate in an amount of about 3.14% w/w, a silicone polymer in an amount of about 0.93% w/w, and a pH modifier in an amount of about 0.19% w/w.

DETAILED DESCRIPTION

Embodiments provided herein related to compositions that treat, reduce, inhibit, or ameliorate cellulite or the appearance of cellulite. In some embodiments, the composition includes a saline solution, a reactive oxygen species, a rheology agent, an emollient, and a pH modifier. Also provided are uses of the compositions in the treatment, reduction, inhibition, or amelioration of cellulite or the appearance of cellulite. The compositions may be provided to a subject for topical application to skin or a region of a body having an appearance of cellulite.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, a "subject" or a "patient" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment, amelioration, inhibition, progression, prophylaxis, or improvement in disease symptoms or who is in need of curative therapy. In some embodiments, a patient is selected who has cellulite or who has the appearance of cellulite. Such identification or selection of said subjects or patients in need can be made through clinical and/or diagnostic evaluation. In some embodiments, a subject is selected who does not have the appearance of cellulite, but who wishes to prevent the appearance of cellulite.

As used herein, the term "treatment" refers to an intervention made in response to a disease, disorder, or physiological condition manifested by a subject, particularly a subject having cellulite or having an appearance of cellulite. The terms treating, treatment, therapeutic, or therapy do not necessarily mean total cure or abolition of the disease or condition. The aim of treatment may include, but is not limited to, one or more of the prophylaxis of cellulite, alleviation or prevention of symptoms, slowing or stopping the progression or worsening of cellulite, curative treatment of cellulite, or the remission of cellulite. In some embodiments, treatment refers to both treatment of cellulite as well as treatment of the physical manifestation or appearance of cellulite. For example, in some embodiments, treatments reduce, alleviate, ameliorate, or eradicate the symptom(s) of the disease and/or provide curative therapy of the disease. In some embodiments, treatment includes administration to a subject that does not have any manifestation of cellulite, but the formulations provided herein are provided for the purpose of preventing the development or onset of cellulite.

The term "therapeutically effective amount" is used to indicate an amount of a composition that elicits the biological or medicinal response indicated. For example, a therapeutically effective amount of composition can be the amount needed to prevent, alleviate, or ameliorate cellulite or the appearance of cellulite. Determination of a therapeutically effective amount is within the capability of those skilled in the art, in view of the disclosure provided herein. The therapeutically effective amount of the composition disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, the term "cellulite" is synonymous with lipodystrophy, an alteration of the appearance of the skin surface resulting from the protrusion of adipose lobules through unstretchable conjunctive tissue. This condition is distinct from obesity and may be present on the abdomen, thighs and buttocks, and especially the thighs and buttocks. Cellulite is also known as adiposis edematosa, dermopanniculosis deformans, status protrusus cutis, gynoid lipodystrophy, or orange peel syndrome.

Some embodiments disclosed herein relate to identifying a region of a body in need of treatment, or skin in need of treatment. As used herein, the term "skin in need of skin cellulite treatment" refers generally to skin, particularly skin of the abdomen, pelvic region, buttocks, thighs, or lower limbs that exhibits a padded and orange-peel appearance generally from the protrusion of adipose lobules through unstretchable conjunctive tissue. According to certain embodiments, skin in need of cellulite treatment includes skin having clinical "Grade 2" cellulite (after skin compression or after muscular contraction there is pallor, decreased temperature and decreased elasticity; no relief alterations at rest; histopathologically, hyperplasia and hypertrophy of the periadipocyte and pericapillary argentaffin fibril framework occurs along with capillary dilatation, microhaemorrhages and increased thickness of the capillary basement membrane) or higher, as described in A. Beatris et al. *Cellulite: A Review Journal of European Academy of Dermatology and Venerology* 2000, 14, 251-262. In some embodiments, a region of a body is identified that does not have manifestations of cellulite, but the formulation is administered for the purpose of prevention the development or onset of cellulite at that region of the body.

Some embodiments provided herein relate to cellulite treatment formulations that include a saline solution, a reactive oxygen species, a rheology agent, an emollient, and a pH modifier. In some embodiments, the cellulite treatment formulation is administered topically to skin having or manifesting cellulite. As used herein, the term "cellulite treatment formulation" refers to embodiments of the formulation as described herein that is used for the treatment, prevention, amelioration, or reduction of cellulite.

In some embodiments, the cellulite treatment formulation is effective as a stand-alone treatment for cellulite, and as such, is administered alone without other treatments, therapies, or agents for treating cellulite. In some embodiments, the cellulite treatment formulation is administered in combination with a cellulite therapy, including laser therapy, shockwave therapy, ultrasound therapy, cellulite creams, scrubs, brushes, massage, or mesotherapy.

As used herein, the term "saline solution" refers to a solution having a quantity of salt. In some embodiments, the saline solution includes a purified or refined salt. In some embodiments, the saline solution includes a raw or unprocessed salt. In some embodiments, the salt is halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt. The salt present in the saline solution can include a number of elements, including actinium, aluminum, antimony, arsenic, astatine, barium, beryllium, bismuth, boron, bromine, cadmium, calcium, carbon, cerium, cesium, chlorine, chromium, cobalt, copper, dysprosium, erbium, europium, francium, fluorine, gadolinium, gallium, germanium, gold, hafnium, holmium, hydrogen, iodine, indium, iridium, iron, lanthanum, lead, lithium, lutetium, magnesium, manganese, mercury, molybdenum, neptunium, neodymium, nickel, niobium, nitrogen, osmium, oxygen, palladium, phosphorus, platinum, plutonium, polonium, potassium, praseodymium, promethium, protactinium, radium, rhenium, rhodium, rubidium, ruthenium, samarium, scandium, selenium, silicon, silver, sodium, strontium, sulfur, tantalum, technetium, tellurium, terbium, thallium, thorium, thulium, tin, titanium, uranium, vanadium, ytterbium, zinc, or zirconium. In some embodiments, the element present in the salt can be present in an amount of less than 0.001 ppm to an amount of greater than 400,000 ppm. In some embodiments, the saline solution includes salt in an amount of 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5, 6, 7, 8, 9, 10, 11, 12, 13, 14, or 15% (w/v), or an amount within a ranged defined by any two of the aforementioned values. In some embodiments, the saline solution includes salt in an amount of 0.05%.

As used herein, the term "reactive oxygen species (ROS)" refers to chemically reactive molecules containing oxygen. Examples include ozone, peroxides, active chlorines, active oxygens, superoxides, active hydrogens, hydroxyl radical, and singlet oxygen. ROS are formed as a natural byproduct of the normal metabolism of oxygen and have important roles in cell signaling and homeostasis. ROS can include, but are not limited to superoxides ($O_2^{*-}$, $HO_2^*$), hypochlorites ($OCl^-$, HOCl, NaClO), hypochlorates ($HClO_2$, $ClO_2$, $HClO_3$, $HClO_4$), oxygen derivatives ($O_2$, $O_3$, $O_4^{*-}$, O), hydrogen derivatives ($H_2$, $H^-$), hydrogen peroxide ($H_2O_2$), hydroxyl free radical ($OH^{*-}$), ionic compounds ($Na^+$, $Cl^-$, $H^+$, $OH^-$, NaCl, HCl, NaOH), chlorine ($Cl_2$), water clusters ($n*H_2O$—induced dipolar layers around ions), and combinations thereof. Some ROS can be electron acceptors and some can be electron donors. In some embodiments, a reactive oxygen species is a hypochlorite.

"Hypochlorous acid", as used herein, refers to a weak acid having the chemical formula HClO. Hypochlorous acid is also known as chloric (I) acid, chloranol, or hydroxidochlorine. Hypochlorite includes ions of hypochlorous acid (for example, $OCl^-$). Salts of hypochlorite are also referred to herein and can include sodium hypochlorite (NaClO), calcium hypochlorite ($Ca(ClO)_2$), or potassium hypochlorite (KClO). Hypochlorite, or acids and salts thereof, may be present in the cellulite treatment formulations described herein in an amount of 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is 0.072% w/v. In some embodiments, the hypochlorite, or salt or acid thereof, is added directly to a cellulite treatment formulation. In some embodiments, the hypochlorite, or acid or salt thereof, is generated in the cellulite treatment formulation by electrolysis. In some embodiments, the final amount of hypochlorous acid is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorous acid in the cellulite treatment formulation is between about 50 to about 100 ppm. In some embodiments, the amount of hypochlorous acid in the cellulite treatment formulation is about 72 ppm.

As used herein, the term "rheology agent" refers to a substance that modulates the viscosity of a cellulite treatment formulation, without modifying other properties of the cellulite treatment formulation. In some embodiments, the rheology agent acts as a thickener by increasing the viscosity of the cellulite treatment formulation. In some embodiments, the rheology agent can include a metal silicate. In some embodiments, the rheology agent is sodium magnesium silicate, a silicate of sodium and magnesium. In some embodiments, sodium magnesium silicate is a synthetic silicate clay, having magnesium and sodium silicate. In some embodiments, a rheology agent is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite, including for example, Laponite XL21™, Laponite RD™, Laponite RDS™, Laponite S482™, Laponite SL25™, Laponite EP™, Laponite JS™, Laponite XLS™, Laponite D™, or Laponite XLG™. The rheology agent may be used in the cellulite treatment formulation in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of rheology agent is about 3% w/v.

As used herein, an "emollient" refers to a compound that soothes the skin. In some embodiments, an emollient is a moisturizer, a cream, a lotion, an oil, a rub, a salve, an unguent, or a balm. In some embodiments, the emollient is a silicone polymer. In some embodiments, the silicone polymer is dimethicone, which is also known as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers also include cyclomethicone, which is a cyclic siloxane. In some embodiments, the silicone polymer used in the cellulite treatment formulation is a blend of dimethicone and cyclomethicone. In some embodiments, the silicone polymer is dimethicone satin, a mixture of low and high molecular weight linear silicones. In some embodiments, the silicone polymer is amodimethicone, cyclodimethicone, cyclomethicone, dimethicone 500, dimethicone satin, iso-dimethicone copolymer, or blends thereof. In some embodiments, a silicone polymer acts as a moisturizer, a slip agent, or a lubricant. The emollient may be present in the cellulite treatment formulation in an amount of about 0.5%, 1%, 5%, 10%, 15%, 20%, 30%, 40%, 50%, or greater w/v %, or in an amount within any two of the aforementioned values or between a range defined by these values. In some embodiments, the amount of silicone polymer is about 5% w/v.

As used herein, the term "pH modifier" refers to an acid, base, or agent that may be used to change or stabilize the pH of the cellulite treatment formulation. A pH modifier may include an agent for modifying the pH of a solution or formulation, such as an acid or a base, including, for example, mineral acids such as hydrochloric acid, phosphoric acid and sulphuric acid, organic acids such as benzoic acid, citric acid, lactic acid, maleic acid, malic acid, tartaric acid, adipic acid, gluconic acid and their salts and bases such as sodium hydroxide and potassium hydroxide. In some embodiments, a pH modifier may include an agent for stabilizing the pH of a solution or formulation at a desired pH, including for example, a buffer such as a sodium acetate, acetate, citrate, or phosphate buffer. In some embodiments, the pH modifier is sodium phosphate monobasic. In some embodiments, the pH modifier is present in an amount of about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or 15% w/v, or an amount within a range defined by any two of the aforementioned values. In some embodiments, the pH modifier is present in an amount of about 0.3% w/v. As used herein, the pH of the composition is the numerical scale to specify the acidity or basicity of the cellulite treatment formulation. In some embodiments, the pH of the cellulite treatment formulation is about 5.0 to about 8.5, such as 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the cellulite treatment formulation is in a range from about 6.0 to about 7.8.

In some embodiments, the cellulite treatment formulations described herein have osmolality measurement values of about 0.5 to 200 mOsm/kg, such as 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 80, 90, 100, 110, 120, 130, 140, 150, 160, 170, 180, 190, or 200 mOsm/kg, or within a range defined by any two of the aforementioned values. In some embodiments, the cellulite treatment formulations have osmolality measurement values of about 3 to 5 mOsm/kg. In some embodiments, the cellulite treatment formulations have osmolality measurement values of about 113 mOsm/kg.

The cellulite treatment formulations described herein may further include an additive known in the art. In some embodiments, the additive includes a compound that improves the formulation for the mode of administration. In some embodiments, the additive improves the efficacy of the formulation. In some embodiments, the additive improves the shelf life of the formulation. In some embodiments, the additive is included for aesthetic purposes to improve the appearance, texture, scent, or feel of the formulation. Exemplary additives for including in a cellulite treatment formulation include moisturizers, humectants, pigments, dyes, pearlescent compounds, nacreous pigments, bismuth oxychloride coated mica, titanium dioxide coated mica, colorants, fragrances, biocides, preservatives, lipolytic agent, diuretics, xanthines (such as caffeine, theophylline, and aminophylline), alpha hydroxy acids, antioxidants, lymphatic drainage agent, antiperspirant agents, exfoliants, hormones, anticellulitic, enzymes, medicinal compounds, vitamins, minerals, electrolytes, alcohols, polyols, polypropylene glycol, anti-adipogenesis agents, retinoids, retinol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays, and combinations thereof.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion.

The cellulite treatment formulations provided herein may be prepared, packaged, or sold in cellulite treatment formulations for topical administration. The cellulite treatment formulations can be filled into suitable packaging (containers) such as, for example, tubes, cartons, capsule, jars, bottles, canisters, squeeze pack, pouches, packages, packets, sacks, tank, or other containers. In some embodiments, the cellulite treatment formulation may be applied directly to skin having or manifesting cellulite. In some embodiments, the cellulite treatment formulation may be applied an applicator, a brush, or other device for application to the skin having or manifesting cellulite.

In some embodiments, the cellulite treatment formulation is applied directly to an area of the subject's skin, for example, a region of skin affected by cellulite, or predisposed to develop cellulite. In other embodiments, the cellulite treatment formulation is applied directly to the area affected by cellulite or predisposed to develop cellulite by one or more of a dropper, an applicator stick, as a mist or aerosol, as a transdermal patch, by wiping with a wipe, or by spreading the cellulite treatment formulation on the area with fingers. The cellulite treatment formulation can be applied to the cellulite-affected area in any suitable therapeutic amount. In some embodiments, the cellulite treatment formulation is administered and/or applied to the cellulite-affected area in ounce units such as from 0.1 oz. to 20 oz. or as desired by the subject. Each application to the cellulite-affected area can be about 0.1 oz., 0.2 oz., 0.3 oz., 0.4 oz., 0.5 oz., 0.6 oz., 0.7 oz., 0.8 oz., 0.9 oz., 1 oz., about 2 oz., about 3 oz., about 4 oz., about 5 oz., about 6 oz., about 7 oz., about 8 oz., about 9 oz., about 10 oz., about 11 oz., about 12 oz., about 16 oz., or about 20 oz. When applied to the cellulite-affected area, it can be applied once, twice, three times, four times or more a day. In one embodiment, the cellulite treatment formulation is applied to the cellulite-affected area at a rate of about 4 oz. twice a day. Likewise, the cellulite treatment formulation can be applied to areas of the subject's skin to prevent the formation of cellulite in similar fashion to the administration to treat cellulite.

Packaging can include single use aliquots in single use packaging such as pouches. The cellulite treatment formulation can be packaged in suitable packaging having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or an amount within a range defined by any two of the aforementioned values. The packaging can also be squeezable pouches having similar volumes.

In some embodiments, packaging may be free of dyes, metal specks, or chemicals that can be dissolved by acids or oxidizing agents. In other embodiments, any bottles, package caps, bottling filters, valves, lines, and heads used in packaging may be specifically rated for acids and oxidizing agents. In some cases, package caps with any organic glues, seals, or other components sensitive to oxidation may be avoided since they could neutralize and weaken the product over time.

As used herein, the term "coadministration" of pharmacologically active compounds refers to the delivery of two or more separate chemical entities or separate therapies, whether in vitro or in vivo. Coadministration refers to the simultaneous delivery of separate agents or therapies; to the simultaneous delivery of a mixture of agents; to the delivery of one agent followed by delivery of a second agent or additional agents; or to the administration of one therapy followed by or concomitant with another therapy. In all cases, agents or therapies that are coadministered are intended to work in conjunction with each other. Similarly, in the context of administration of more than one compound, the term "in combination" refers to a concomitant delivery of one compound with one or more compounds. The compounds may be administered in combination by simultaneous administration or administration of one compound before or after administration of another compound.

In some embodiments, the cellulite treatment formulation for treating an cellulite as described herein is administered alone, in the absence of other treatments, therapies, or agents for the treatment of cellulite. In some embodiments, the cellulite treatment formulation for treating cellulite as described herein administered in combination with a cellulite therapy, including laser therapy, shockwave therapy, ultrasound therapy, cellulite creams, scrubs, brushes, massage, mesotherapy, liposuction, or subcision, or other therapy used for the treatment of cellulite.

In some embodiments, the cellulite treatment formulation provided herein is used in combination with laser therapy. As used herein, laser therapy includes the use of optical energy, such as a diode laser or solid state laser to target an area affected with cellulite. In some embodiments, the laser therapy includes cellulaze. As used herein, cellulaze includes insertion of a laser tube under the skin of the subject in an area affected with cellulite, and is used to melt the pockets of fat, and soften the connective tissue.

In some embodiments, the cellulite treatment formulation provided herein is used in combination with shockwave therapy. As used herein, shockwave therapy refers to a non-surgical, non-invasive treatment using high-frequency acoustic shockwaves, which focus on the collagen structure of cellulite-affected skin, causing a remodeling of the collagen fibers. Shockwave therapy can include focused shockwave, short focused shockwave, long focused shockwave, unfocused shockwave, linear unfocused shockwave, or radial unfocused shockwave.

In some embodiments, the cellulite treatment formulation provided herein is used in combination with ultrasound therapy. As used herein, ultrasound therapy includes cryolipolysis, a non-invasive method for localized destruction of subcutaneous adipocytes.

In some embodiments, the cellulite treatment formulation provided herein is administered in combination with an anti-cellulite product, such as a cream or other composition used in the treatment of cellulite. In some embodiments, the cellulite treatment formulation as provided herein is administered prior to application of the cream or other composition. In some embodiments, the cream or other composition is administered prior to administration of the cellulite treatment formulation.

In some embodiments, the cellulite treatment formulation provided herein is administered in combination with a cellulite scrub. As used herein, a cellulite scrub refers to a cleansing of the skin affected with cellulite with an exfoliating body scrub or an exfoliating brush used to smooth the skin to improve the appearance of cellulite.

In some embodiments, the cellulite treatment formulation provided herein is administered in combination with a cellulite massage. As used herein a cellulite massage refers to a massage technique to increase circulation and to improve the appearance of cellulite. Massage can include mechanical devices, or pressotherapy, such as endermologie, subdermal massage, rolling massage, suction massage, or other types of massage, and can be used in combination with the cellulite treatment formulations described herein.

In some embodiments, the cellulite treatment formulation is used in combination with mesotherapy. As used herein mesotherapy refers to a therapy that includes injection of various treatment solutions through the skin to treat cellulite. The injection results in increased circulation and the potential for fat oxidation, and includes injection of compounds such as aminophylline, hyaluronic acid, Novocain, plant extracts, vitamins, antifibrotics, lypolytics, or anti-inflammatories.

In some embodiments, the cellulite treatment formulation is used in combination with liposuction, tumescent liposuction, or lipolysis, which target adipose tissue in the subdermal and deep fat regions of the body. These techniques may include removing the fat cells once they are disrupted, or leaving them to be resorbed by the body's immune/lymphatic system. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient.

In some embodiments, the cellulite treatment formulation is used in combination with subcision. This technique involves the insertion of a relatively large gauge needle subdermally in the region of dimpling or scarring, and then mechanically manipulating the needle below the skin to break up the fibrous septae in the subdermal region.

In some embodiments, the "purity" of any given agent (for example, hypochlorous acid or a buffer) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

In some embodiments, the cellulite treatment formulation may be applied directly into the skin, and therefore, the cellulite treatment formulation may be formulated for topical application. Accordingly, the cellulite treatment formulation may have any suitable form for topical administration.

In some embodiments the formulation is in the form of a cream, a hydrogel, a lotion, a gel, a serum, a liquid, a foam, a mist, or an ointment. In some embodiments, the cellulite treatment formulation may be applied by injection into an area of the body having or manifesting cellulite, such as by intradermal or subcutaneous administration.

The cellulite treatment formulations described herein are used for the treatment, prevention, amelioration, or reduction of cellulite or the manifestation of cellulite. In some embodiments, the formulation is administered by topically applying a therapeutic amount of the formulations to areas of the skin that are affected by cellulite. In other embodiments, the formulation is administered by topically applying a therapeutic amount of the formulations to areas of the skin that are affected by adiposis edematosa, dermopanniculosis deformans, status protrusus cutis, gynoid lipodystrophy, and/or orange peel syndrome. In other embodiments, the formulation is administered by topically applying a therapeutic amount of the formulations to areas of the skin to prevent the formation of cellulite. For example, the formulation can be applied to areas of the skin that are affected by cellulite such as the pelvic region, lower limbs, abdomen, buttocks, and/or thighs. In some cases, the formulation can be applied to areas of the skin to prevent the formation of cellulite such as the pelvic region, lower limbs, abdomen, buttocks, and/or thighs. The pelvic region, lower limbs, abdomen, buttocks, and/or thighs are predisposed to the development of cellulite. The formulation may be applied to these regions to treat cellulite, to reduce the manifestation of cellulite, or to prevent the development of cellulite.

In some embodiments, the cellulite treatment formulations are administered to a subject by topical application of the formulation to a region of the body affected by cellulite, or a region of the body where the prevention of cellulite is desirable. In some embodiments, the cellulite treatment formulation is administered by massaging the formulations into the region of the body until the formulation is absorbed.

In some embodiments, administration of the cellulite treatment formulation increases skin elasticity, reduces the appearance of cellulite, reduces fat nodules, reduces subcutaneous fat nodularity, inhibits adipogenesis, or increases lipolysis in adipocytes.

In some embodiments, treating cellulite comprises applying the formulation to skin affected by cellulite to increase elasticity of the skin at the treated area. In some cases, the elasticity of an area of cellulite-affected skin can be measured before treatment. The affected area can then be treated and the elasticity of the treated area can be measured. In other cases, the treated area can exhibit an increase in elasticity. In some instances, the increase in elasticity of the treated area can be up to about 1%, about 2%, about 3%, about 4%, about 5%, about 6%, about 7%, about 8%, about 9%, about 10%, about 15%, about 20%, about 25%, about 30%, about 35%, and about 40%. In other instances, the increase in elasticity may be seen after 1 day to 1 year, such as after 1 day, after 2 days, after 3 day, after 4 days, after 5 days, after 6 days, after 1 week, after 2 weeks, after 3 weeks, after 4 weeks, after 1 month, after 2 months, after 3 months, after 4 months, after 5 months, after 6 months, after 7 months, after 8 months, after 9 months, after 10 months, after 11 months, or after 1 year.

In some embodiments, reducing the appearance of cellulite includes reducing the severity of cellulite based on the manifestation of cellulite, such that the manifestation of cellulite decreases from hard sub-surface nodules and pronounced lumpiness of the skin and striations, to small bumps or depressions, and no cellulite present. The reduced appearance of cellulite can be assessed by measuring the appearance of the skin at the treated region, the reduction of thigh diameter, the reduction of the fatty layer thickness, skin firmness, surface smoothness, The disclosure is generally described herein using affirmative language to describe the numerous embodiments. The disclosure also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

Preparation of Cellulite Treatment Formulations

The following example describes an embodiment of a cellulite treatment formulation and methods of making the formulation.

A cellulite treatment formulation was prepared with the ingredients as provided in Table 1. The ingredients provided below were added to saline solution, with a final pH adjusted to 6.5-7.0. The saline solution was prepared with 0.05% salt.

TABLE 1

Cellulite Treatment Formulation

| Ingredient | Final % wt/vol | Role in Formulation |
| --- | --- | --- |
| Saline Solution (0.05% salt) | 91.378 | Base |
| Laponite XLG | 3.25 | Rheology agent |
| Dimethicone Satin | 5 | Emollient |
| Sodium Hypochlorite (4.99%) | 0.072 | Reactive oxygen species |
| Sodium Phosphate Monobasic | 0.3 | pH modifier |

Refined salts, such as tables salts can be used to prepare the saline solution, which include the components listed in Table 2.

TABLE 2

Refined salt components used in saline solution

| Element | Quantity (ppm) |
| --- | --- |
| Aluminum | 0.747 |
| Antimony | 0.014 |
| Arsenic | 0.039 |
| Barium | 0.012 |
| Beryllium | 0.038 |
| Bismuth | 0.005 |
| Bromide | 81.414 |
| Cadmium | 0.007 |
| Calcium | 10.625 |
| Chromium | 0.027 |
| Cobalt | 0.001 |
| Copper | 0.053 |
| Germanium | 0.081 |
| Iodide | <0.001 |
| Iron | 0.639 |
| Lead | 25.908 |
| Magnesium | 3.753 |
| Manganese | 0.040 |

TABLE 2-continued

Refined salt components used in saline solution

| Element | Quantity (ppm) |
|---|---|
| Mercury | 0.013 |
| Molybdenum | 0.007 |
| Nickel | 0.016 |
| Phosphorus | 3.690 |
| Potassium | 60.756 |
| Selenium | 0.202 |
| Silver | 0.002 |
| Sodium | 391,290 |
| Strontium | 0.230 |
| Tin | 0.166 |
| Zinc | 0.791 |

The salt composition of Table 2 is refined table salt, and the quantity of elements was determined by inductively couple plasma mass spectrometry (ICP-MS). Teachings in the art suggest that only purified, refined salts may be used in a saline solution having reactive oxygen species, such as hypochlorite, and that raw or unprocessed salts are incompatible for use in a saline solution having reactive oxygen species. Thus, not only can raw, unprocessed salts be used in the saline solution, but raw, unprocessed salts result in raw salt compositions that function unexpectedly superior to compositions prepared using refined salts. The components for the raw salt composition using raw salt are provided in Table 3, in three separate salt compositions.

TABLE 3

Raw salt components used in saline solution

| Element | Composition 1 | Composition 2 Quantity (ppm) | Composition 3 |
|---|---|---|---|
| Aluminum | 114.8 | 32.473 | 241.700 |
| Antimony | 0.022 | 0.013 | 0.026 |
| Arsenic | 0.066 | 0.046 | 0.076 |
| Barium | 0.664 | 0.343 | 7.615 |
| Beryllium | 0.051 | 0.030 | 0.070 |
| Bismuth | 0.005 | 0.004 | 0.006 |
| Bromide | 56.006 | 70.607 | 7.789 |
| Cadmium | 0.017 | 0.010 | 0.024 |
| Calcium | 2101.000 | 1290.000 | 1860.000 |
| Chromium | 0.207 | 0.195 | 0.175 |
| Cobalt | 0.033 | 0.013 | 0.058 |
| Copper | 0.116 | 0.090 | 0.279 |
| Germanium | 0.072 | 0.085 | 0.092 |
| Iodide | <0.001 | <0.001 | <0.001 |
| Iron | 81.722 | 23.292 | 141.400 |
| Lead | 0.093 | 0.077 | 0.210 |
| Magnesium | 1944.000 | 1304.000 | 217.900 |
| Manganese | 1.911 | 1.040 | 11.804 |
| Mercury | 0.016 | 0.009 | 0.012 |
| Molybdenum | 0.011 | 0.014 | 0.037 |
| Nickel | 0.096 | 0.086 | 0.113 |
| Phosphorus | 5.125 | 3.548 | 9.541 |
| Potassium | 1728.000 | 1174.000 | 149.300 |
| Selenium | 0.269 | 0.235 | 0.226 |
| Silver | 0.004 | 0.002 | 0.006 |
| Sodium | 388690.000 | 391706.000 | 390600.000 |
| Strontium | 32.223 | 18.328 | 11.251 |
| Tin | 0.169 | 0.135 | 0.177 |
| Zinc | 1.261 | 1.045 | 1.883 |

The raw salt compositions provided in Table 3 were analyzed by ICP-MS to determine the quantity of elements. The salt compositions used were various types of raw sea salt (compositions 1 and 2—Himalayan pink sea salt; composition 3—sea salt).

The cellulite treatment formulation described in Table 1 is useful for the treatment, prevention, amelioration, or reduction of cellulite or the manifestation of cellulite, especially when the saline solution is prepared using a salt provided in Table 3, or other forms of raw salt described herein. The formulation may be used alone in or in combination with cellulite treatment therapies. Furthermore, the formulation may be applied directly to the region affected by cellulite or may be applied with a device, such as an applicator. In some embodiments, the formulation may be prepared as a gel, a cream, a salve, a serum, a foam, a paste, a lotion, an ointment, or other composition suitable for topical administration to the skin. In some embodiments, the formulation may be prepared for injection, such as by intradermal or subcutaneous administration to a region of skin affected by cellulite.

Example 2

Additional Cellulite Treatment Formulations

The following example describes an embodiment of a cellulite treatment formulation.

A cellulite treatment formulation including salts in variety was prepared with the ingredients as provided in Table 4. The ingredients provided below were added to water, with a final pH adjusted to 6.5-7.0.

TABLE 4

Salt Cellulite Treatment Formulation

| Ingredient | Final % wt/wt |
|---|---|
| Water | 95.53% |
| Salt | 0.05% |
| Metal Silicate | 3.14% |
| Silicon Polymer | 0.93% |
| Reactive Oxygen Species | 0.16% |
| pH Modifier | 0.19% |

The salt cellulite composition in Table 4 included a salt of halite, table salt, common salt, curing salt, flake salt, Epsom salt, sea salt, Alaea salt (or Hawaiian sea salt), Alpenbergkern salt, Anglesey Sea salt, Celtic sea salt, Dead Sea salt, Himalayan sea salt (including Himalayan pink sea salt), Kalahari salt, Maras salt, Murray River salt flakes, Namibian salt pearls, Persian blue fine salt, Polish mine salt, primordial sea salts, Sal de Tavira, Sale Marino di Trapani, Sel de Guérande, South African Sea salt, Utah salt, black lava salt, brine, rock salt, red rock salt, fleur de sel, or kosher salt, or combinations thereof.

The cellulite treatment formulation described in Table 4 is useful for the treatment, prevention, amelioration, or reduction of cellulite or the manifestation of cellulite. The formulation may be used alone in or in combination with cellulite treatment therapies. Furthermore, the formulation may be applied directly to the region affected by cellulite or may be applied with a device, such as an applicator. In some embodiments, the formulation may be prepared as a gel, a cream, a salve, a serum, a foam, a paste, a lotion, an ointment, or other composition suitable for topical administration to the skin. In some embodiments, the formulation may be prepared for injection, such as by intradermal or subcutaneous administration to a region of skin affected by cellulite.

Example 3

Cellulite Treatment Formulations for Reducing Cellulite

The following example describes the use of the cellulite treatment formulations provided herein to treat, prevent, and reduce cellulite or the appearance of cellulite.

The cellulite treatment formulation as described in Examples 1 or 2 is used to treat, prevent, reduce, or ameliorate cellulite or the appearance of cellulite.

Female subjects are selected to evaluate the formulation. Subjects are selected based on their cellulite intensity in a region affected with cellulite. A 5-point grading scale is used to rate the cellulite severity of each subject prior to administration of the cellulite treatment formulation. The scale ranges from 0 to 4, being 0=No cellulite; 1=Small bumps or depressions; 2=Striations and bumps; 3=Pronounced lumpiness of the skin and striations; 4=All of the above plus hard sub-surface nodules.

All subjects have the absence of any visible skin diseases that might be confused with a skin reaction from the test material and are in general good health with no known allergies, especially to cosmetic or toiletry products; have no evidence of acute or chronic disease; are not pregnant or lactating; are not on any diet or weight reduction program; and are not on any regular exercise program (immediately prior to or during the course of the study).

At baseline each subject receives a visual examination conducted by a qualified technician and receives a score for the degree of cellulite. On the same day, subjects are administered a cellulite treatment formulation. The treatment is repeated daily over the course of the study. All subjects tolerate the topical formulation during the course of the study as measured by dermatological and clinical criteria. For each volunteer, a test area (treated area) and a control area (untreated area) are selected on the cellulite-affected area of the skin. The topical formulation is applied daily to the test area. The topical formulation is not applied to the control area. There are no undesired or pathological skin reactions in the test area. The subjects are also divided into appropriate control groups to test the efficacy of the cellulite treatment formulations against control formulations, including refined salt formulations (as described herein) or no treatment.

The degree of cellulite is observed by digital photography of the test skin area, and evaluations are given according to the following scale: 0=No visible cellulite; 1=Very little visible cellulite, no dimpling; 2=Visible cellulite, evidence of shallow dimpling; 3=Easily visible cellulite, moderate to pronounced dimpling; 4=Extremely visible cellulite, heavy and deep dimpling. In addition, the following data are collected at the beginning of the study and after the study: cutometry (skin elasticity) measurements of the test area; ultrasound examination of the test skin area; and depth and width measurements of the adipose lobules. Each subject also completes a participant questionnaire following completion of the study.

Subjects are instructed to discontinue the use of their normal anti-cellulite products or therapies, to avoid introducing any new products for treating cellulite during the study, and to not be on any diet or weight reduction program or on any regular exercise program immediately prior to or during the course of the study.

Following the final treatment, subjects return for a final visual evaluation. The cellulite evaluation is made by comparison of the values before and after the treatment with the cellulite treatment formulations. The efficacy of the cellulite treatment formulations is evaluated based on skin firmness, reduction of thigh diameter, reduction of fatty layer thickness, skin hydration, surface smoothness, and reduction in the appearance of cellulite.

Example 4

Comparative Cellulite Treatment Formulations

The following example compares the cellulite treatment formulation described in Example 1 with refined salt cellulite treatment formulations. A comparison of the formulations is provided in Table 5.

TABLE 5

Comparative Cellulite Treatment Formulations

| Ingredient | Final % wt/vol of Example 1 Formulation | Final % wt/vol of refined salt Formulation |
| --- | --- | --- |
| Saline Solution | 91.378 (0.05% raw salt components of Table 3) | 96.51 (0.07% refined salt components of Table 2) |
| Laponite XLG | 3.25 | 3.25 |
| Dimethicone Satin | 5 | — |
| Sodium Hypochlorite (4.99%) | 0.072 | 0.040 |
| Sodium Phosphate Monobasic | 0.3 | 0.2 |

The cellulite treatment formulations as described in Table 5 are compared for efficacy in treating, preventing, reducing, or ameliorating cellulite or the appearance of cellulite. Subjects are administered a composition, as described in Example 3. The subjects are divided into groups, including a no treatment group, a group administered the formulation of Example 1 or Example 2, and a group administered a refined salt formulation. The formulation of Example 1 or Example 2, which includes raw salt components, unexpectedly exhibits superior treatment properties in comparison to the refined salt formulation. Subjects administered the formulation of Example 1 or Example 2 exhibit superior improvements in the appearance of cellulite as compared to subjects that received the refined salt formulation and in comparison to subjects that received no treatment.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or claims, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of reducing an appearance of cellulite in a subject in need thereof, the method comprising:
   identifying a region of a body having cellulite;
   topically applying to the region of the body a composition comprising:
   an electrolyzed saline solution comprising a salt;
   a reactive oxygen species comprising hypochlorite;
   a rheology agent;
   dimethicone in an amount of about 0.5% to about 10% w/v; and
   a pH modifier,
   wherein the salt is Himalayan sea salt present in an amount of about 0.01% to about 15% w/v, and the hypochlorite is in an amount of about 60 to about 100 ppm, and
   wherein the composition has an osmolality measurement ranging from about 3 to about 5 mOsm/kg; and
   massaging the composition into the region of the body having cellulite until absorbed,
   thereby reducing the appearance of cellulite.

2. The method of claim 1, wherein reducing the appearance of cellulite comprises increasing skin elasticity.

3. The method of claim 1, wherein reducing the appearance of cellulite comprises reducing subcutaneous fat nodularity.

4. The method of claim 1, wherein reducing the appearance of cellulite comprises increasing lipolysis in adipocytes.

5. The method of claim 1, wherein the composition comprises:
   salt in an amount of about 0.01% to about 1% w/v;
   hypochlorite in an amount of about 60 to about 80 ppm;
   sodium magnesium silicate in an amount of about 0.5% to about 10% w/v;
   dimethicone in an amount of about 0.5% to about 10% w/v; and
   sodium phosphate monobasic in an amount of about 0.05% to about 5% w/v.

6. The method of claim 5, wherein the salt is raw, unprocessed salt.

7. The method of claim 1, wherein the reactive oxygen species is hypochlorite present in an amount of about 65 to about 75 ppm.

8. The method of claim 1, wherein the pH modifier is sodium phosphate monobasic present in an amount of about 0.05% to about 5% w/v.

9. The method of claim 1, wherein the rheology agent is a metal silicate.

10. The composition of claim 9, wherein the metal silicate is sodium magnesium silicate present in an amount of about 0.5% to about 10% w/v.

11. The method of claim 1, wherein the composition is administered daily to the region of the body having cellulite.

12. The method of claim 1, wherein the salt is present in an amount of about 0.05% w/v.

13. The method of claim 1, wherein the hypochlorite is present in an amount of about 72 ppm.

14. The method of claim 1, wherein the rheology agent is present in an amount of about 3.25% w/v.

15. The method of claim 1, wherein the emollient is present in an amount of about 5% w/v.

16. The method of claim 1, wherein the pH modifier is present in an amount of about 0.3% w/v.

17. The method of claim 1, wherein the composition is formulated as a cream, foam, gel, serum, lotion, mousse, ointment, paste, solution, spray, stick, or suspension.

* * * * *